United States Patent
Moreau et al.

(10) Patent No.: US 6,685,959 B1
(45) Date of Patent: Feb. 3, 2004

(54) PHARMACEUTICAL COMPOSITIONS COMPRISING 2-ISOXAZOLES-8-AMINOTETRALIN DERIVATIVES

(75) Inventors: Jacques Pierre Moreau, Upton, MA (US); Béatrice Guimbert, Huest (FR); Marc Pellet, Conde sur Iton (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 0 days.

(21) Appl. No.: 10/069,804

(22) PCT Filed: Apr. 26, 2000

(86) PCT No.: PCT/FR00/01099

§ 371 (c)(1),
(2), (4) Date: Jan. 30, 2002

(87) PCT Pub. No.: WO00/64444

PCT Pub. Date: Nov. 2, 2000

(30) Foreign Application Priority Data

Apr. 26, 1999 (FR) .............................. 99 05268

(51) Int. Cl.[7] .................................. A61K 9/70
(52) U.S. Cl. .................. 424/449; 424/443; 424/447; 514/359; 514/374; 514/378
(58) Field of Search ................ 424/443, 447, 424/449; 514/359, 374, 378

(56) References Cited

FOREIGN PATENT DOCUMENTS

| EP | 0 498 590 A1 | * 8/1992 |
|---|---|---|
| EP | 0565274 | 10/1993 |
| EP | 0579507 | 1/1994 |
| WO | 9015047 | 12/1990 |
| WO | 9913879 | 3/1999 |

* cited by examiner

*Primary Examiner*—Thurman K. Page
*Assistant Examiner*—Konata M. George
(74) *Attorney, Agent, or Firm*—Muserlian, Lucas and Mercanti

(57) ABSTRACT

The invention relates to novel pharmaceutical compositions comprising 2-isoxazole-8-aminotetralin derivatives. The invention more specifically relates to compositions in the form of a patch comprising a therapeutically efficacious amount of a derivative of 2-isoxazole-8-aminotetraline, especially 1,2,3,4-tetrahydro-8(5-isoxazolyl)N-N-diisopropyl-2-naphtalenamine. The invention also relates to a 2-isoxazole-8-aminotetralin derivative, especially 1,2,3,4-tetrahydro-8-(5-isoxazolyl)-N,N-diisopropyl-2-naphtalenamine, which is used to produce a medicament which can be administered transdermally to treat irritable bowel syndrome.

11 Claims, No Drawings

PHARMACEUTICAL COMPOSITIONS COMPRISING 2-ISOXAZOLES-8-AMINOTETRALIN DERIVATIVES

This application is a 371 of PCT/FR00/01099 filed Apr. 26, 2000.

The present invention relates to novel pharmaceutical compositions containing derivatives of 2-isoxazoles-8-aminotetralines.

Derivatives of 2-isoxazoles-8-aminotetralines and their use as medicaments have in particular been described by Eli Lilly in the European Patent Applications EP 385 658 and EP 471 515, as well as in the European Patent EP 498 590 which describes in particular 1,2,3,4-tetrahydro-8-(5-isoxazolyl)-N,N-diisopropyl-2-naphthalenamine. The use of these compounds for treating irritable bowel syndrome has moreover been described in the European Patent Application EP 579 507.

However, none of these patents describes the administration of these products by transdermal route.

Now the Applicant has just discovered that compositions can be used for a topical administration comprising a derivative of 8-isoxazole-2-aminotetraline. In particular, the Applicant has perfected an adhesive polymer system (or "patch") comprising in its structure said derivative of 8-isoxazole-2-aminotetraline.

Therefore the invention relates to a matrix or reservoir pharmaceutical composition for an administration by topical route comprising at least one derivative of 8-isoxazole-2-aminotetraline in a therapeutically effective quantity and one or more pharmaceutically acceptable excipients.

By derivative of 8-isoxazole-2-aminotetraline, is meant in particular all those which have been described in the patents mentioned previously. Said derivative of 8-isoxazole-2-aminotetraline can be presented in the form of the free base or in the form of a pharmaceutically acceptable salt.

By pharmaceutically acceptable salt, is meant in particular the addition salts of inorganic acids such as the hydrochloride, sulphate, phosphate, diphosphate, hydrobromide and nitrate or of organic acids such as the acetate, maleate, fumarate, tartrate, succinate, citrate, lactate, methane sulphonate, p-toluenesulphonate, pamoate, oxalate and stearate. The salts formed from bases such as sodium or potassium hydroxide are also included in the field of the present invention, when they are of use. For other examples of pharmaceutically acceptable salts, reference can be made to "Pharmaceutical salts", *J Pharm. Sci.* 66:1 (1977).

Preferably, the derivative of 8-isoxazole-2-aminotetraline will be in the form of a pharmaceutically acceptable salt.

Different forms of matrices or reservoirs can be used. These include in particular creams, emulsions, gels or also substances which can be gelled in air. Preferably, a patch will be used which will contain in its matrix the 8-isoxazole-2-aminotetraline derivative. Said patch can be presented in different forms: reservoir; matrix on adhesive polymer; DIA patch (i.e. "Drug In Adhesive"), in other words a patch in the form of a single adhesive polymer layer in which the active ingredient is distributed; or finally a multilayered patch. These various forms of patch are in particular described in the following reference work: *Technology Advances in drug Delivery*, PJB Publications Ltd., p. 85–100 (1998). When the composition is in the form of a patch, the said DIA form will be preferred.

The excipients can be polymers or copolymers or simply monomers. Preferably, the composition will incorporate adhesive polymers or copolymers such as elastomers of the polyethylenevinylacetate (EVA) type, polymers or copolymers based on styrene, polyisobutylene or acrylic polymers or copolymers, and in particular methacrylic copolymers.

When the polymer or copolymer excipients are included in a composition according to the invention, one or more plasticizer agents can also be present. These plasticizer agents include, for example, tributylacetyl citrate or any other pharmaceutically acceptable plasticizer agent known to a person skilled in the art.

When the composition according to the invention is in the form of an aqueous gel, a gelling agent is present preferably in a proportion of 20 to 50%. Gelling agents which can be used for topical compositions according to the invention include in particular cellulose derivatives and in particular hydroxyl-propyl-methyl cellulose (HPMC), or poloxamers (i.e. copolymers of polyethylene and propylene glycol), in particular Lutrol® F127 (BASF).

The topical compositions according to the invention can moreover include other excipients in order to facilitate the transdermal passage of the derivative of 8-isoxazole-2-aminotetraline, in other words promoters of transdermal absorption, and in particular alcohols or polyols such as ethanol, 1,3-butanediol, polyethyleneglycols (PEG), the esters of fatty acids, in particular the triglycerides of caprylic and capric acids and in particular Miglyol® (Hüls, Marl, Germany), or other surfacants or amphiphilic substances known to a person skilled in the art. Among the promoters of transdermal absorption, ethanol or the esters of fatty acids such as Miglyol® will be preferred.

Finally, the compositions according to the invention can also include where appropriate and in particular when they are presented in the form of an aqueous gel, a preservative agent, preferably propylene glycol. Similarly, they can also include an anti-oxidizing agent, and in particular ethylenediamihetetracetic acid (EDTA).

Among the derivatives of 8-isexazole-2-aminotetraline, 1,2,3,4-tetrahydro-8-(5-isoxazolyl)-N,N-diisopropyl-2-naphtlialenamine will be quite particularly preferred.

The preparation of the derivatives of 8-isoxazole-2-aminotetraline, and in particular of 1,2,3,4-tetrahydro-8-(5-isoxazolyl)-N,N-diisopropyl-2-naphthalenamine is described in Patents or Patent Applications EP 385 658, EP 471 515, EP 498 590 and EP 979 507. These compounds can be salified if necessary according to the usual methods known to a person skilled in the art.

A topical pharmaceutical composition according to the invention will preferably contain between approximately 5 and 80 mg, more preferably between approximately 5 and 50 mg, and more particularly between approximately 5 and 20 mg, for example approximately 5 mg of the derivative of 8-isoxazole-2-aminotetraline, this mass being calculated with respect to said derivative in the form of a free base. This dose should allow the daily treatment of a patient to be ensured, but it is the attending doctor who will definitively decide on the frequency of application.

Finally, in order to ensure an optimum level of transdermal passage, the pH of the topical pharmaceutical composition according to the invention will preferably be comprised between 7 and 9.5, more preferentially between 8 and 9.5 when the derivative of 8-isoxazole-2-aminotetraline is in the form of a free base. When the derivative of 8-isoxazole-2-aniinotetraline is in the form of a salt, the pH of the topical pharmaceutical composition according to the invention will preferably be comprised between 5 and 7.5, and more preferentially between 5.5 and 7.

The invention also relates to the use of a derivative of 8-isoxazole-2-aminotetraline, and in particular 1,2,3,4- tetrahydro-8-(5-isoxazolyl)-N,N-diisopropyl-2-naphthalenamine, in order to produce a medicament allowing a transdermal administration, in particular in the treatment of irritable bowel syndrome.

Unless defined in another manner, all the technical and scientific terms used here have the same meaning as that commonly understood by an ordinary specialist in the field to which the invention belongs. Similarly, all publications, patent applications, all patents and all other references mentioned here are incorporated by way of reference.

The following examples are presented to illustrate the pharmaceutical compositions described above and must in no case be considered as a limit to the scope of the invention.

EXAMPLE 1

A patch intended for the transdermal administration of 1,2,3,4-tetrahydro-8-(5-isoxazolyl)-N,N-diisopropyl-2-naphthalenarnine was prepared from a copolymer of methacrylate and ammonioalkyl according to the operating method described hereafter.

20 g of acetone, 2 g of isopropyl alcohol and 11 g of ethanol are mixed together in a receptacle. The mixture is agitated and 39 g of EUDRAGIT® E 100 (supplier: Röhm GmbH, Darmstadt, Germany) is added in small portions and at regular intervals over a period of one and a half hours, the agitation being sufficiently vigorous so that the EUDRAGIT® E 100 does not deposit. Then 19 g of tributylacetyl citrate is added and agitation is carried out for another 20 minutes. 20 g of 1,2,3,4-tetrahydro-8-(5-isoxazolyl)-N,N-diisopropyl-2-naphthalenamine (prepared as described in the European Patent EP 498 590) is added in several goes, agitation being maintained for 30 minutes. Finally, while vigorously agitating the mixture, 1.5 g of succinic acid is added in several portions and agitation is maintained for another 20 minutes.

The solution obtained is then spread at the rate of 100 g/m$^2$ on a carrier sheet (15 $\mu$m thick, Revtrans MN, Tricon GmbH, Freiburg-im-Breisgau, Germany). The layer of polymer is dried for 10 minutes with a flow of 1500 m$^3$/h of air at 60° C. (recycling with 80 m$^3$/h escape).

The polymer obtained can then be cut to form patches with a surface of approximately 15 cm$^2$, which can be used for dispensing a daily dose.

EXAMPLE 2

A patch intended for the transdermal administration of 1,2,3,4-tetrahydro-8-(5-isoxazolyl)-N,N-diisopropyl-2-naphthalenamine was prepared from a copolymer of methacrylate and ammonioalkyl according to the operating method described in Example 1, except that 10 g of Miglyol® 812 (Hüls, Marl, Germany) was added by portions between the addition of 1,2,3,4-tetrahydro-8-(5-isoxazolyl)-N,N-diisopropyl-2-naphthalenamine and the addition of succinic acid and that after this addition of Miglyol® 812, the mixture was agitated for an extra 20 minutes.

EXAMPLE 3

A patch intended for the transdermal administration of 1,2,3,4-tetrahydro-8-(5-isoxazolyl)-N,N-diisopropyl-2-naphthalenamine was prepared from a methacrylate and ammonioalkyl copolymer according to an operating method analogous to that described in Example 1, except that the 20 g of 1,2,3,4-tetrahydro-8-(5-isoxazolyl)-N,N-diisopropyl-2-naphthalenarnine is replaced with 22.44 g of 1,2,3,4-tetrahydro-8-(5-isoxazolyl)-N,N-diisopropyl-2-naphthalenamine hydrochloride.

EXAMPLE 4

A gel intended for the transdermal administration of 1,2,3,4-tetrahydro-8-(5-isoxazolyl)-N,N-diisopropyl-2-naphthalenamine was prepared from an aqueous dispersion of hydroxy-propyl-methyl-cellulose (HPMC) according to the operating method described below (in order to prepare 100 g of gel).

Composition of the gel:

| | |
|---|---|
| 1,2,3,4-tetrahydro-8-(5-isoxazolyl)-N,N-diisopropyl-2-naphthalenamine hydrochloride | 3 g |
| Propylene glycol | 4 g |
| HPMC | 30 g |
| Purified water | qsf 100 g |

Preparation of the gel:

First, an aqueous solution (solution I) is prepared by solubilizing 3 g of 1,2,3,4-tetrahydro-8-(5-isoxazolyl)-N,N-diisopropyl-2-naphthalenamine hydrochloride in 4 g of propylene glycol and 8 g of purified water. The solution obtained in this way is then filtered on a 10 $\mu$m filter. Solution I is obtained.

An aqueous dispersion of HPMC is then prepared under vacuum by mixing 30 g of HPMC with 55 g of purified water. Still under agitation, the mixture is heated at a temperature of 50–60° C. for 20 minutes, until a gel is obtained having a homogeneous appearance (gel II).

Solution I is added in portions to gel II, then the mixture is left under vacuum, under agitation and at 50–60° C. for 20 minutes in order to obtain 100 g of medicament.

The medicament is homogeneised by passing through a die (die homogenizer).

After cooling down, the gel obtained in this way can be distributed into tubes. Each application will consist of a pea-sized amount of approximately 1 g.

EXAMPLE 5

A gel intended for the transdermal administration of 1,2,3,4-tetrahydro-8-(5-isoxazolyl)-n,n-diisopropyl-2-naphthalenamine was prepared, according to the operating method described in example 4, except that the poloxamer Lutrol® F127 (BASF) was used as gelling agent.

What is claimed is:

1. A matrix or reservoir pharmaceutical composition for topical administration of at least one derivative of 8-isoxazole-2-aminotetraline in a therapeutically effective amount, a plasticizer agent and at least one pharmaceutically acceptable polymer or copolymer excipient in the form of a patch.

2. A matrix or reservoir pharmaceutical composition for topical administration of at least one derivative of 8-isoxazole-2-aminotetraline in a therapeutically effective amount and at least one pharmaceutically acceptable excipient in the form of a patch in the form of a single adhesive polymer layer in which the derivative 8-isoxazole-2-aminotetraline is distributed.

3. A composition of claim 1 wherein it contains a preservative agent.

4. A matrix or reservoir pharmaceutical composition for topical administration of at least one derivative of 8-isoxazole-2-aminotetraline in a therapeutically effective amount, an anti-oxidizing agent and at least one pharmaceutically acceptable excipient in the form of a patch.

5. A composition of claim 1 wherein the derivative of 8-isoxazole-2-aminotetraline is present in the form of a pharmaceutically acceptable salt.

6. A matrix or reservoir pharmaceutical composition for topical administration of 8-isoaxazole-2-aminotetraline is 1,2,3,4-tetrahydro-8-(5-isoaxazolyl)-N,N-diisopropyl-2-naphthalenamine or one of its pharmaceutically acceptable salts in a therapeutically effective amount and of at least one of pharmaceutically excipient in the form of a patch.

7. A matrix or reservoir pharmaceutical composition for topical administration of at least one derivative of 8-isoxazole-2-aminotetraline in a therapeutically effective amount, a promoter of transdermal absorption and at least one pharmaceutically acceptable excipient in the form of a patch.

8. A composition of claim 7 wherein the promoter of transdermal absorption is selected from the group consisting of alcohols, polyols, the esters of fatty acids, and other surfactants and amphiphilic substances.

9. A composition of claim 1 containing between 5 and 80 mg of the derivative of 8-isoxazole-2-aminotetraline, this mass being calculated with respect to said derivative in the form of a free base.

10. A method of treating irritable bowel syndrome in warm-blooded animals comprising transdermally administering to warm-blooded animals in need thereof a matrix or reservoir pharmaceutical composition for topical administration of at least one derivative of 8-isoxazole-2-aminotetraline in a therapeutically effective amount and at least one pharmaceutically acceptable excipient in the form of a patch.

11. The method of claim 10 wherein the 8-isoxazole-2-aminotetraline derivative is 1,2,3,4-tetrahydro-8-(5-isoxazolyl)-N,N-diisopropyl-2-naphthalenamine or its pharmaceutically acceptable salts.

* * * * *